US011273285B2

(12) United States Patent
Montidoro (10) Patent No.: US 11,273,285 B2
(45) Date of Patent: Mar. 15, 2022

(54) ANCILLARY DEVICE FOR DETACHING IMPLANTS

(71) Applicant: DePuy Synthes Products, Inc., Raynham, MA (US)

(72) Inventor: Tyson Montidoro, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 287 days.

(21) Appl. No.: 16/269,828

(22) Filed: Feb. 7, 2019

(65) Prior Publication Data
US 2020/0254213 A1 Aug. 13, 2020

(51) Int. Cl.
*A61M 25/00* (2006.01)
*A61M 25/01* (2006.01)

(52) U.S. Cl.
CPC .... *A61M 25/0012* (2013.01); *A61M 25/0147* (2013.01)

(58) Field of Classification Search
CPC ................. A61M 25/0147; A61M 25/015
USPC ................... 29/234, 244, 251, 33 F
See application file for complete search history.

(56) References Cited

U.S. PATENT DOCUMENTS

| | | | |
|---|---|---|---|
| 3,018,531 A * | 1/1962 | Arsenault | F16G 11/12 24/134 R |
| 3,087,236 A * | 4/1963 | Paytas | B25B 27/026 29/244 |
| D402,030 S | 12/1998 | Roberts et al. | |
| D402,031 S | 12/1998 | Roberts et al. | |
| D439,336 S | 3/2001 | Najmi | |
| 6,360,430 B1 * | 3/2002 | Stepan | H02G 1/1265 29/33 F |
| 6,391,037 B1 | 5/2002 | Greenhalgh | |
| D463,555 S | 9/2002 | Etter et al. | |
| D469,870 S | 2/2003 | Niermann et al. | |
| D483,475 S | 12/2003 | Kirwan et al. | |

(Continued)

FOREIGN PATENT DOCUMENTS

| | | |
|---|---|---|
| EP | 2 366 364 A1 | 9/2011 |
| JP | 1514152 S | 12/2014 |

(Continued)

OTHER PUBLICATIONS

US D855,181 S, 07/2019, Khan et al. (withdrawn)
Extended European Search Report issued in corresponding European Patent Application No. 20 15 5881 dated May 20, 2020.

*Primary Examiner* — Christopher M Koehler
(74) *Attorney, Agent, or Firm* — Troutman Pepper Hamilton Sanders LLP (57) ABSTRACT

A pull wire can be retracted from a catheter by using a retraction system having an opening sized to pass through the pull wire and engage the catheter, two clamps positioned around the pull wire, a shuttle on which the clamps are mounted, and a slider having at least one contact for contacting and moving one or both clamps. To retract the pull wire, the slider can be moved proximally, the contact(s) can engage one or both clamps on the shuttle, the clamps can move so that the clamps come together and grip the pull wire, and the slider can then be moved further proximally to translate the shuttle, clamps, and pull wire proximally thereby extracting the pull wire from the catheter. The shuttle and slider can subsequently be moved distally without translating the pull wire.

9 Claims, 10 Drawing Sheets

(56) References Cited

U.S. PATENT DOCUMENTS

| | | |
|---|---|---|
| D490,125 S | 5/2004 | Myall et al. |
| D492,995 S | 7/2004 | Rue et al. |
| 6,773,448 B2 | 8/2004 | Kusleika et al. |
| D496,730 S | 9/2004 | Morawski et al. |
| 6,849,081 B2 | 2/2005 | Sepetka et al. |
| D530,680 S | 10/2006 | Fox et al. |
| 7,147,618 B2 | 12/2006 | Kurz |
| D535,026 S | 1/2007 | Griffin et al. |
| D537,528 S | 2/2007 | Christensen et al. |
| D568,475 S | 5/2008 | Sandel et al. |
| D571,010 S | 6/2008 | Cota |
| 7,419,498 B2 | 9/2008 | Opolski et al. |
| D586,916 S | 2/2009 | Faulkner et al. |
| D598,070 S | 8/2009 | Sneddon et al. |
| D612,061 S | 3/2010 | Ruf |
| D616,095 S | 5/2010 | Kim et al. |
| D621,042 S | 8/2010 | Ruf |
| D622,406 S | 8/2010 | Russell, II et al. |
| 7,785,361 B2 | 8/2010 | Nikolchev et al. |
| D628,293 S | 11/2010 | Ruf |
| D628,695 S | 12/2010 | Ruf |
| D634,843 S | 3/2011 | Kim et al. |
| 7,942,894 B2 | 5/2011 | West |
| 8,151,425 B2 * | 4/2012 | Cossart ............... B25B 23/101 |
| | | 29/281.1 |
| D665,909 S | 8/2012 | Dodd et al. |
| D677,380 S | 3/2013 | Julian et al. |
| D678,512 S | 3/2013 | Bow |
| D679,014 S | 3/2013 | Jayaraj |
| D682,092 S | 6/2013 | Morawski et al. |
| D703,707 S | 4/2014 | Foster et al. |
| D719,255 S | 12/2014 | Ohashi |
| D719,651 S | 12/2014 | Hoffmann et al. |
| 8,911,487 B2 | 12/2014 | Bennett et al. |
| D736,923 S | 8/2015 | Snow |
| D737,440 S | 8/2015 | Shabaz |
| D739,020 S | 9/2015 | Kumar |
| D740,422 S | 10/2015 | Herfort |
| D740,630 S | 10/2015 | Hasenmayer |
| D741,483 S | 10/2015 | Solingen et al. |
| 9,173,771 B2 | 11/2015 | Keller |
| D744,638 S | 12/2015 | Bow |
| 9,232,992 B2 | 1/2016 | Heidner |
| D749,717 S | 2/2016 | Kobida et al. |
| D753,301 S | 4/2016 | Fisken et al. |
| D755,383 S | 5/2016 | Pfister et al. |
| D759,246 S | 6/2016 | Allen et al. |
| D765,841 S | 9/2016 | Schuerg |
| D765,842 S | 9/2016 | Schuerg |
| D766,432 S | 9/2016 | Schuerg |
| D767,760 S | 9/2016 | Suwito et al. |
| D770,044 S | 10/2016 | Fisken et al. |
| D770,618 S | 11/2016 | Fisken et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,554,940 B2 | 1/2017 | Haffner et al. |
| D779,053 S | 2/2017 | Kobida et al. |
| D780,306 S | 2/2017 | Bow |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,592,151 B2 | 3/2017 | Rangel-Friedman et al. |
| 9,615,832 B2 | 4/2017 | Bose et al. |
| 9,615,951 B2 * | 4/2017 | Bennett ............... A61F 2/95 |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| D789,453 S | 6/2017 | Walker et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| D791,318 S | 7/2017 | Jutila et al. |
| 9,693,852 B2 | 7/2017 | Lam et al. |
| 9,700,262 B2 | 7/2017 | Janik et al. |
| 9,700,322 B2 | 7/2017 | Dias et al. |
| 9,700,399 B2 | 7/2017 | Acosta-Acevedo |
| D794,192 S | 8/2017 | Schuerg |
| D794,193 S | 8/2017 | Schuerg |
| D794,194 S | 8/2017 | Schuerg |
| D794,790 S | 8/2017 | Shi |
| D795,424 S | 8/2017 | Sloss |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,717,627 B2 | 8/2017 | Kuzma et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| D799,040 S | 10/2017 | Melnikoff et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| D802,769 S | 11/2017 | Robertson et al. |
| 9,808,599 B2 | 11/2017 | Bowman et al. |
| D806,230 S | 12/2017 | Johnson et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| D818,584 S | 5/2018 | Lee et al. |
| D828,542 S | 9/2018 | Bow |
| D834,702 S | 11/2018 | Evans et al. |
| D837,975 S | 1/2019 | Protasiewicz et al. |
| D838,360 S | 1/2019 | Protasiewicz et al. |
| D839,417 S | 1/2019 | Funakoshi |
| D841,164 S | 2/2019 | Flowers et al. |
| D846,738 S | 4/2019 | Kalina, Jr. et al. |
| D847,334 S | 4/2019 | Amano |
| 10,278,720 B2 | 5/2019 | Marczyk et al. |
| D851,755 S | 6/2019 | Nazzaro et al. |
| D844,784 S | 8/2019 | Swick et al. |
| D861,864 S | 10/2019 | Amano |
| D879,960 S | 3/2020 | Melnikoff et al. |
| 10,780,218 B2 | 9/2020 | Novakovic et al. |
| D901,683 S | 11/2020 | Kalina, Jr. et al. |
| D903,100 S | 11/2020 | Stats et al. |
| D910,836 S | 2/2021 | Sandberg et al. |
| D911,521 S | 2/2021 | Swift et al. |
| 2003/0083613 A1 | 5/2003 | Schaer |
| 2005/0070820 A1 | 3/2005 | Boutilette et al. |
| 2006/0064151 A1 | 3/2006 | Guterman |
| 2007/0179520 A1 | 8/2007 | West |
| 2008/0281350 A1 | 11/2008 | Sepetka |
| 2010/0324649 A1 | 12/2010 | Mattsson et al. |
| 2011/0238147 A1 * | 9/2011 | Bennett ............... A61F 2/95 |
| | | 623/1.11 |
| 2012/0029607 A1 * | 2/2012 | McHugo ............... A61F 2/966 |
| | | 623/1.11 |
| 2012/0283768 A1 | 11/2012 | Cox et al. |
| 2013/0048338 A1 | 2/2013 | Suzuki et al. |

(56) References Cited

U.S. PATENT DOCUMENTS

| | | |
|---|---|---|
| 2013/0087596 A1 | 4/2013 | Fontayne et al. |
| 2014/0135812 A1 | 5/2014 | Divino et al. |
| 2014/0200607 A1 | 7/2014 | Sepetka et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367857 A1 | 12/2017 | Bennett et al. |

FOREIGN PATENT DOCUMENTS

| | | |
|---|---|---|
| JP | 1557500 S | 8/2016 |
| JP | 1677819 S | 1/2021 |
| WO | WO 98/11846 A1 | 3/1998 |

\* cited by examiner

ANCILLARY DEVICE FOR DETACHING IMPLANTS

FIELD OF INVENTION

The present invention generally relates to medical devices, and more particularly, to deploying intraluminal implants.

BACKGROUND

Numerous intravascular implant devices and clot capture devices are known in the field. Many are deployed and manipulated mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants can also be implanted via similar systems that combine one or more catheters and wires. Devices that can be released, deployed, or otherwise manipulated by mechanical means vary greatly in design but can employ a similar delivery catheter and wire system.

Many such catheter-based delivery systems include a catheter and an inner elongated member (or members) such as an inner catheter or wire, the catheter and inner elongated member(s) configured to retain an implant in the catheter until the time for release of the implant. These systems can be actuated by retracting or pulling one or more of the inner elongated member(s) relative to the catheter. Such a wire or inner elongated member is referred to herein as a "pull wire". Precise deployment of the implant is crucial for the successful treatment of vascular and luminal abnormalities. For some applications, complications can arise if a pull wire is pulled proximally and then subsequently pushed distally. It is an object of the invention to provide systems, devices, and methods for reducing complications in such applications.

SUMMARY

Example systems and methods for retracting a pull wire from a mechanical intravascular implant device can address the above needs. In some examples, a pull wire can be retracted from a catheter with a retraction system having two clamps mounted to a sliding shuttle and a slider having at least one contact for contacting and moving one or both of the two clamps. The pull wire can be positioned between gripping areas on the two clamps when the clamps are in an open position. Then, when the slider is moved proximally, the contact (or contacts) on the slider can engage one or both clamps on the shuttle, causing at least one of the clamps to move so that the gripping areas come together and grip the pull wire. The slider can then be moved further proximally to translate the sliding shuttle, clamps, and pull wire proximally. The retraction system can have a tapered opening through which the pull wire can freely pass but the catheter cannot pass, so that while the pull wire is pulled proximally, the catheter is held in place.

An example retraction system for withdrawing an inner elongated member of an implantation delivery system from a catheter can have a first clamp, a second clamp, a shuttle on which the clamps are mounted, a contact, and a slider on which the contact is mounted. The shuttle and the slider can each be translated in a proximal and a distal direction. The retraction system can be configured so that a first translation of the slider in the proximal direction translates the first contact proximally to apply a first force from the first contact to the first clamp, the first force moving the first clamp to move the clamps from an open position to a closed position. The first clamp can have a first griping area, and the second clamp can have a second gripping area. In the open position the first gripping area and the second gripping area can be positioned to allow the inner elongated member of the implantation delivery system to pass through. In the closed position the first gripping area and the second gripping area can be positioned to engage the inner elongated member. The retraction system can be configured so that a second translation of the slider in the proximal direction can proximally translate the first clamp arm and the second clamp arm to proximally withdraw the inner elongated member from the catheter of the implantation delivery system while the catheter is held in place by the retraction system.

The slider of the retraction system can include a second contact. The retraction system can be configured so that the first translation of the slider translates both the first and the second contact proximally to apply a second force from the second contact to the second clamp, the second force moving the second clamp from the open position to the closed position. The first force and the second force can be applied to the clamps simultaneously to move the clamps in concert from the open position to the closed position.

The retraction system can include a housing sized to be hand-held, and the shuttle and the slider can be slidably mounted to the housing.

The retraction system can include a distal mounting block, a proximal mounting block, and a rail extending between the distal mounting block and the proximal mounting block. The shuttle and the slider can each be slidably mounted on the rail. The distal mounting block and the proximal mounting block can be mountable to a flat surface, can be mounted or rested on a patient, and/or can be mounted within a hand-held retractor. The distal mounting block can have a first opening for receiving the implantation delivery system. The first opening can be integrated into a housing of the hand-held retractor. The first opening can be sized to inhibit proximal movement of the catheter and to allow the inner elongated member to pass through.

The retraction system can include a return spring positioned to apply a return spring force between the slider and the distal mounting block. The return spring force can be sufficient to move the slider in the distal direction in relation to the distal mounting block. The retraction system can be configured so that a third translation of the slider in the distal direction can cause the first contact to move and disengage the first clamp. The retraction system can be configured so that the third translation of the slider in the distal direction can cause both the first and second contacts to move and disengage the first and second clamps.

The retraction system can have a first spring positioned to apply a first spring force on the first clamp, and the first spring force can be sufficient to move the first clamp from the closed position to the open position when the first contact is disengaged from the first clamp. The first clamp can be rotatable about a first rotating joint. The first clamp can be attached to the shuttle at the first rotating joint. The first spring force can produce a first rotation of the first clamp about the first rotating joint.

The second clamp can be stationary, or it can be movable. If movable, the second clamp can be movable as a mirror image of the first clamp, and the pair of clamps can be movable from the open position to the closed position and vice versa by movement of both clamps. The retraction system can include a second contact on the slider that is positioned to engage the second clamp. The first and second contacts can engage and/or disengage the first and second clamps simultaneously. The retraction system can include a second spring positioned to apply a second spring force on the second clamp, and the second spring force can be sufficient to move the second clamp from the closed position to the open position when the second contact is disengaged from the second clamp. The second clamp can be rotatable about a second rotating joint. The second clamp can be attached to the shuttle at the second rotating joint. The second spring force can produce a second rotation of the second clamp about the second rotating joint.

An example system for deploying an implant can include an entrance, a pair of clamp arms, a shuttle, and a slider. The entrance can be sized to receive an elongated release member of an implant delivery system and inhibit proximal movement of a catheter of the implant delivery system. At least one clamp arm of the pair of clamp arms can be rotatable from an open position to a closed position. In the open position, the pair of clamp arms can be disengaged from the elongated release member and in the closed position the pair of clamp arms can be engaged with the elongated release member. The pair of clamp arms can be mounted to the shuttle, and the shuttle can be translatable in a proximal direction and a distal direction. The slider can be translatable in the proximal and distal directions to engage or disengage one or both of the rotatable clamp arms so that upon an initial proximal movement of the slider, the slider contacts the rotatable clamp arm(s) and provides a force to rotate the rotatable clamp arm(s) to move the clamp arms from the open position to the closed position. The slider can be further translated proximally to translate the shuttle and the pair of clamp arms proximally, and the proximal translation of the pair of clamp arms can proximally withdraw the elongated release member from the catheter.

The system can include a housing sized to be hand-held, and the shuttle and the slider can be slidably mounted to the housing.

The example system can include a distal mounting block, a proximal mounting block, and a rail extending between the distal and proximal mounting blocks. The shuttle and slider can each be slidably mounted on the rail. The system can include four rails.

The system can include an entrance that is a tapered opening in the distal mounting block. The tapered opening can be sized to allow the elongated release member to pass through and to engage a proximal end of the catheter.

The system can be configured such that a distal translation of the slider can cause the slider to separate from the shuttle and to disengage from the rotatable clamp arm(s).

The system can include at least one spring, and each spring can be positioned to apply a force to one or both of the rotatable clamp arms. The force from each spring can move each spring-loaded clamp arm so that the pair of clamp arms moves from the closed position to the open position or from the open position to the closed position.

An example method can include steps for deploying an implant. The method can include providing an implant delivery system, the implant delivery system including a catheter, an inner elongated member positioned within the catheter and extending proximally from the catheter. The method can include providing a retraction system comprising an entrance, a slider, a shuttle, and a pair of clamp arms mounted to the shuttle.

The method can include positioning the pair of clamp arms in an open position. The method can include positioning the inner elongated member through the entrance of the retraction system and between the pair of open clamp arms such that clamp arms are disengaged from the inner elongated member. The method can include engaging the catheter of the implant delivery system to the entrance of the retraction system.

The method can include moving the slider proximally through a first distance to contact at least one of the clamp arms. The method can include moving the slider proximally through a second distance to move the clamp arm(s) that is/are in contact with the slider, thereby moving the pair of clamp arms from the open position to a closed position, such that in the closed position, the clamp arms are engaged with the inner elongated member. The clamp arm(s) that is/are in contact with the slider can each be rotatable about a respective rotating joint, and the step of moving the slider proximally through the second distance can further include rotating the clamp arm(s) in contact with the slider about each respective rotating joint.

The method can include moving the slider proximally through a third distance to move the shuttle and the clamp arms proximally, thereby withdrawing the inner elongated member proximally from the catheter while maintaining the position of the catheter.

The method can include moving the slider distally through a fourth distance to disengage the slider form the clamp arm(s). The position of the inner elongated member can be maintained as the slider is moved distally. This step can further include maintaining the position of the shuttle as the slider is moved distally through the fourth distance.

The retraction system can include one or more springs, and the method can include providing a force from each of the springs to each of the movable clamp arms to move the clamp arms from the closed position to the open position when the slider is not engaged with the clamp arm(s).

The retraction system provided can further include a distal mounting block, a proximal mounting block, and a rail. The method can further include extending the rail between the distal mounting block and the proximal mounting block, slidably mounting the slider to the rail, and slidably mounting the shuttle to the rail proximal to the slider.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Mechanical implant delivery systems, clot capture systems, and other systems actuated by an inner tube/outer tube assembly in which the inner tube translates relative to the outer tube can utilize one or more hypotubes or pull wires within a guide catheter, and the hypotubes and/or pull wires can be available for manipulation at a proximal end of the delivery system to deploy an implant, capture a clot, or perform other intralumenal treatment at a distal end of the delivery system. Examples of implants that can be delivered mechanically include embolic elements, stents, grafts, drug delivery implants, flow diverters, filters, stimulation leads, sensing leads, or other implantable structures deliverable through a microcatheter. Example retraction systems described herein can interface with the proximal end of the delivery system to aid the user in detaching and/or deploying an implant or capturing a clot at the distal end.

The example retraction systems can generally include a system of components that can retract the inner hypotube(s) and/or pull wire(s) without producing distal movement of the hypotube(s)/pull wire(s) and their subcomponents during and after release of an implant. The example retraction system can include a mechanical slider that a user can translate in a single linear motion. The slider, when retracted, can apply a torque to one or both clamp arms in a pair of clamp arms. The torque can move the clamp arms to compress and grip onto a proximal inner tube or pull wire. The gripped elongated member can be translated with respect to the main delivery tube by proximally sliding the slider. The retraction system can include an indicator that indicates to the user when the slider has reached its end of travel, or example the indicator can be a tactile and/or auditory indicator. The travel distance of the slider can be sized such that the implant is released as the slider approaches, or reaches, its end of travel. The indicator can indicate to the user that the implant has been released.

The retraction system can include one or more springs that are positioned to cause the clamps to open and release the engaged elongated member when the user releases pressure on the slider. The retraction system can include a mechanism (such as a spring or known means) for returning the retraction system to a starting or initial position.

Potentially the retraction system can provide a more reliable detachment of an embolic or other implant on a mechanical detachment system compared to traditional retraction systems. More reliable detachment can be achieved by retracting a pull wire, inner tube, pull wire/inner tube assembly, or other elongated member proximally without producing advancement or distal movement of implant delivery system components during and after release of an implant.

Figure 1A:
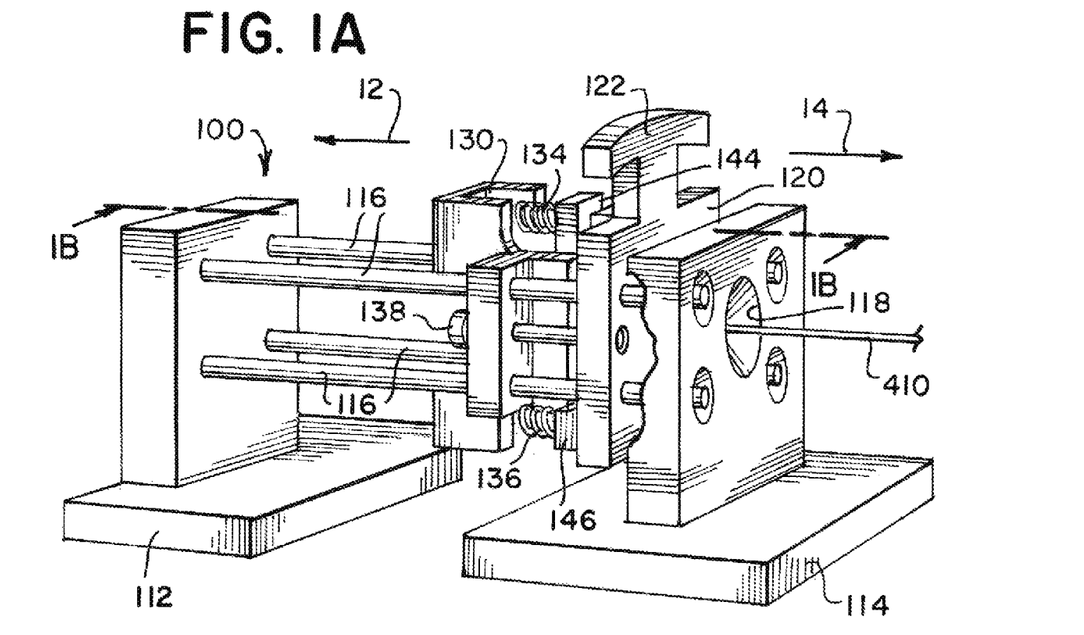
FIGS. 1A and 1B are illustrations of an exemplary retraction system according to aspects of the present invention, FIG. 1B being a cross-sectional view of FIG. 1A.
Figure 1B:
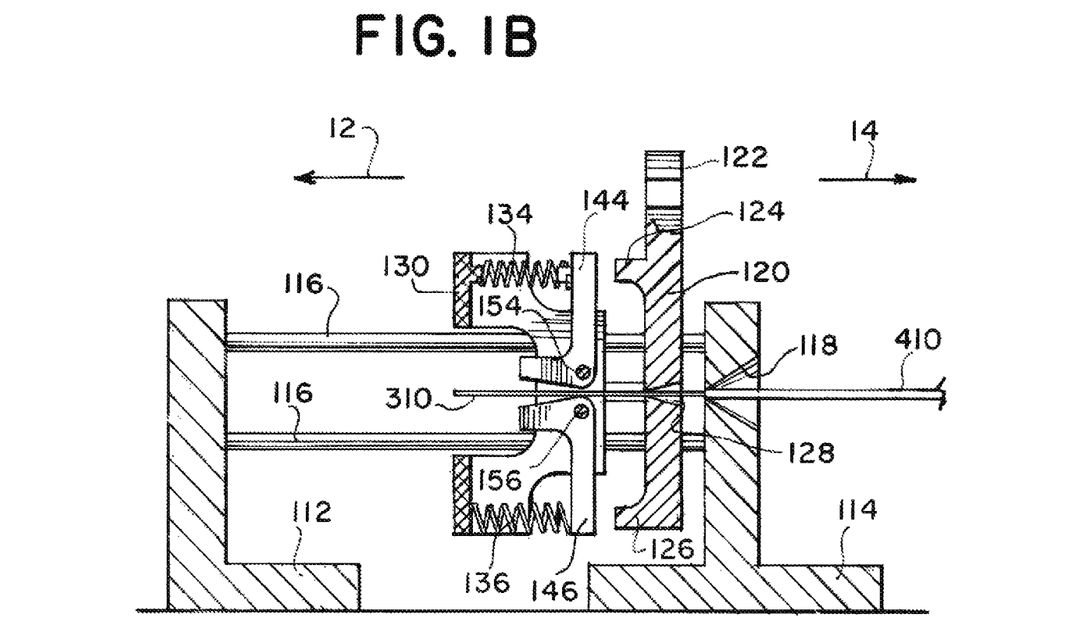

FIGS. 1A and 1B are illustrations of an exemplary retraction system 100. FIG. 1B is a cross-sectional view of FIG. 1A. FIGS. 1A and 1B show components of the exemplary retraction system 100 in a starting or initial position with a proximal portion of an implant delivery system having a delivery catheter 410 and an inner tube, pull wire, or inner tube and pull wire assembly 310 ("pull wire") positioned in the retraction system 100 and ready for deployment of an implant (or intraluminal procedure).

The retraction system 100 can include a shuttle 130 having clamps 144, 146 for grasping the pull wire 310, a slider 120 movable by a user, one or more slide rails 116 over which the shuttle 130 and the slider 120 can slide, a distal mounting block 114 for receiving the implant delivery system and providing an anchor for the slide rails 116, and proximal mounting block 112 for anchoring the slide rails 116. The retraction system 100 can be configured to receive a delivery catheter 410 and the pull wire 310 of the implant delivery system, grasp the pull wire 310, engage a proximal end of the delivery catheter 410, and pull the pull wire 310 to retract the pull wire 310 from the delivery catheter 410.

The system 100 can be mounted within a hand-held retractor, can be mounted on a flat surface, or can be mounted on a patient. When the system 100 is mounted within a hand-held retractor or handle, the distal mounting block 114 and the proximal mounting block 112 can be integral parts of a housing or shell of the hand-held retractor. The system 100 can include one or more rails 116 that extend between the distal mounting block 114 and the proximal mounting block 112. When the system 100 is mounted within a hand-held retractor, the rail or rails 116 can extend between portions of a housing of the hand-held retractor and/or be integrated into the housing. The rails 116 can be grooves or tracks in the housing or handle shell. The retraction system 100 can include an opening 118 that is sized to allow the pull wire 310 to pass through but inhibit the delivery catheter 410 from passing through. The opening 118 can be tapered for ease of aligning the pull wire 310 and delivery catheter 410 in relation to the system 100, for ease of inserting the pull wire 310 into the system 100, and/or for ease of securely engaging a range of various sized delivery catheters. The opening 118 can be positioned in the distal mounting block 114.

The implant delivery system 300 can be inserted into a self-aligning tapered opening 118 at the entrance of the retraction system 100. The main delivery catheter 410 can have a hard stop at the entrance 118 of the device, and the inner elongated member 310 can be free to enter the retraction system 100. The inner elongated member 310 can be inserted through the distal mounting block 114, slider 120, and shuttle 130.

The slider 120 can include an opening 128 sized to allow the pull wire 310 to pass through. The slider 120 can include a handle 122 that can be grasped by a user or otherwise directly or indirectly manipulated by the user to move the slider 120. The slider 120 can include one or more contacts 124, 126 for engaging and providing a force against one or more of the clamp arms 144, 146 on the shuttle 130. The slider 120 can include a first contact 124 and a second contact 126 that are respectively positioned to engage and provide a first force and a second force against a first clamp arm 144 and a second clamp arm 146. The slider 120 can be mounted on the rails 116, and the slider 120 can move along the rails 116 in a distal direction 12 and a proximal direction 14.

The shuttle 130 can include a pair of clamp arms 144, 146 that are movable from an open position that allows the pull wire 310 to pass through to a closed position that grips the pull wire 310. The clamps 144, 146 can be mounted to the shuttle 130, and one or both clamps 144, 146 can be movable. One or both clamps 144, 146 can be mounted to the shuttle 130 at a rotating joint 154, 156. Each clamp 144, 146 can rotate about its respective rotating joint 154, 156, the rotation moving the clamps 144, 146 from the open position to the closed position, and vice versa. FIGS. 1A and 1B illustrate the clamps 144, 146 in the open position and an inner tube or pull wire 310 positioned between the clamps 144, 146 so that pull wire 310 is not engaged by the clamps 144, 146. A first spring 134 can be mounted to the shuttle 130, and the first spring 134 can apply a first spring force to the first clamp arm 144. The first force can be provided in a direction to move and/or maintain the first clamp 144 in the open position. A second spring 136 can be mounted to the shuttle 130, and the second spring 136 can apply a second spring force to the second clamp arm 146. The second force can be provided in a direction to move and/or maintain the second clamp 146 in the open position. The shuttle 130 can be mounted to the rails 116, and the shuttle 130 can move along the rails in the proximal direction 12 and the distal direction 14. The shuttle 130 can be positioned proximal the slider 120. One or more spacer pins 138 can be slidably mounted through the shuttle 130, and the spacer pins can be manipulated to maintain a set spacing between the slider 120 and the shuttle 130, or the spacer pins 138 can be allowed to move so that the spacing between the slider 120 and the shuttle 130 can be collapsed.

Figure 2:
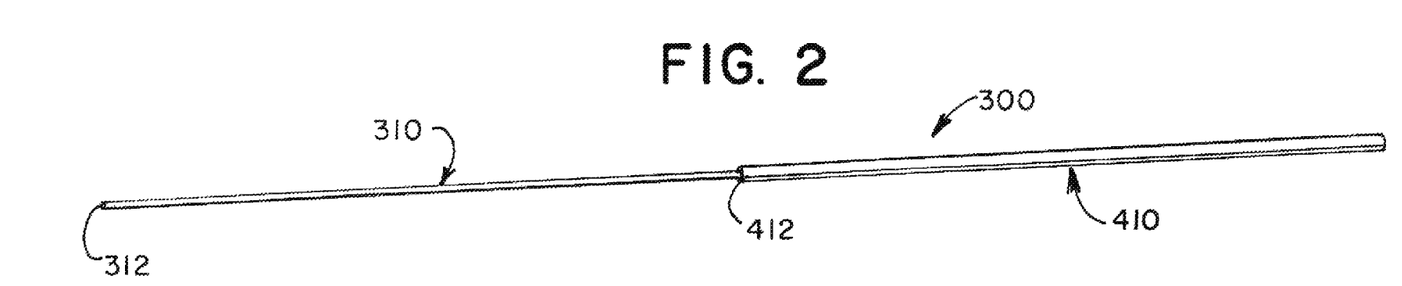
FIG. 2 is an illustration of an implant delivery system that can be used together with an exemplary retraction system according to aspects of the present invention.

FIG. 2 is an illustration of a proximal portion of a mechanical implant delivery system 300 (or other intralumenal treatment device) that can be used together with an exemplary retraction system 100. The delivery system 300 can include an inner tube, pull wire, inner tube and pull wire assembly, or some other elongated member 310 designed to be retracted from a proximal end 412 of a delivery catheter 410 during an intralumenal treatment. The elongated member 310 can be grasped by the retraction system 100 near its proximal end 312 and pulled proximally from the delivery catheter 410.

Figure 3A:
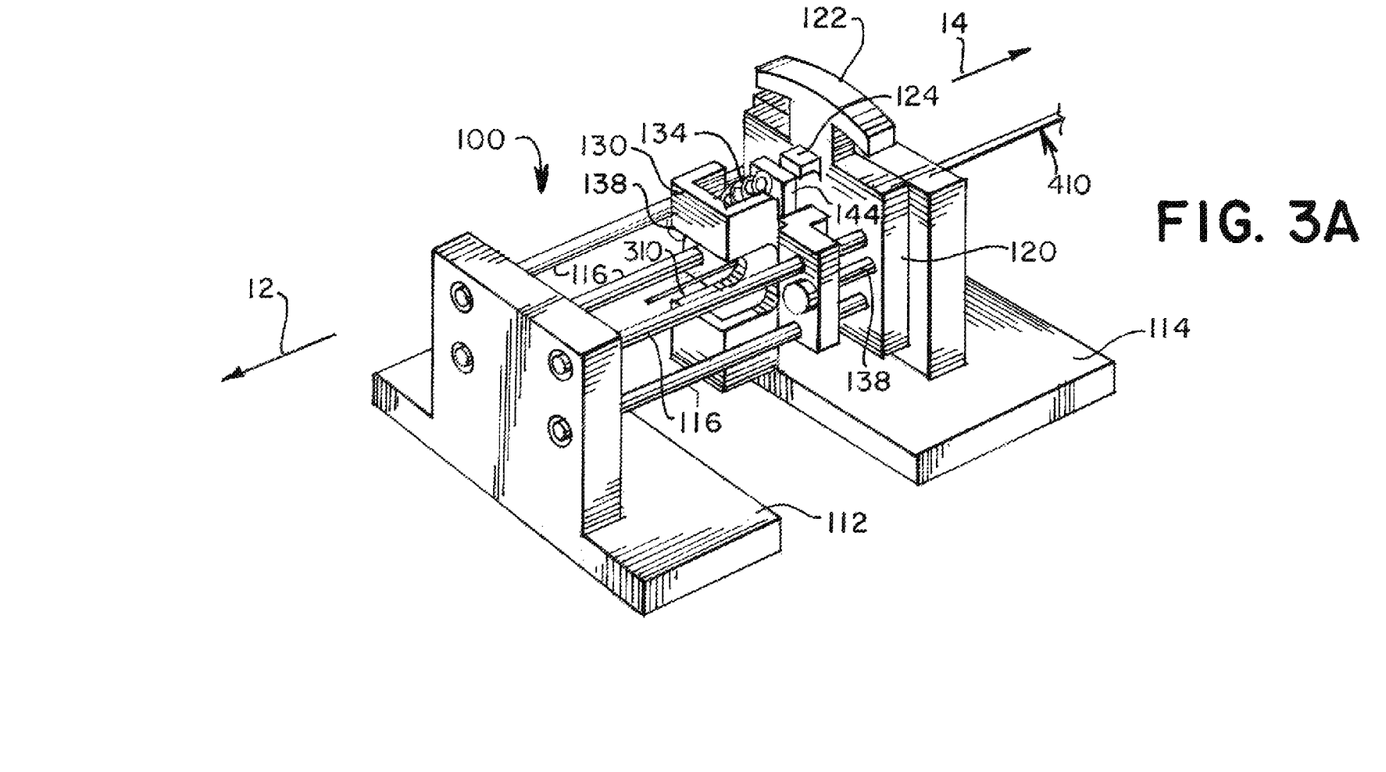
FIGS. 3A and 3B are illustrations of an exemplary retraction system with a proximal portion of an implant delivery system positioned in the retraction system, the retraction system and implant delivery system positioned prior to retraction of a pull wire from the implant delivery system according to aspects of the present invention.
Figure 3B:
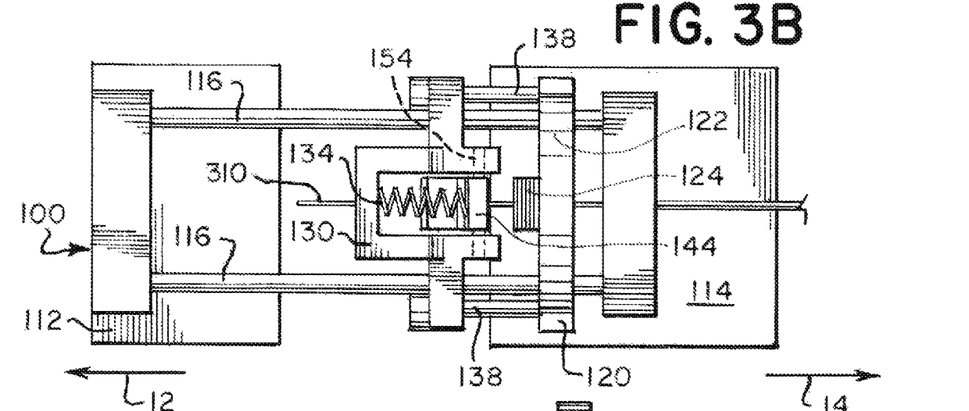

FIGS. 3A and 3B are illustrations of an exemplary retraction system 100 with an implant delivery system 300 positioned in the retraction system 100, the retraction system 100 and implant delivery system 300 positioned prior to retraction of a pull wire 310 from the implant delivery system 300. FIG. 3A is a perspective view. FIG. 3B is a top-down view. Referring collectively to FIGS. 3A and 3B, in the initial position, a slider 120 can be positioned at a distal end of its length of travel, and a shuttle 130 can be positioned near the slider 120 and disengaged from the slider 120 at a distal end of the shuttle's length of travel. The length of travel for both the slider 120 and the shuttle 130 can be determined at least in part by the positioning of a distal mounting block 114, a proximal mounting block 112, and one or more rails 116. A spacer pin 138 or multiple spacer pins 138 can be slidably mounted through the shuttle 130 and extended to maintain a spacing between the slider 120 and the shuttle 130.

Figure 4A:
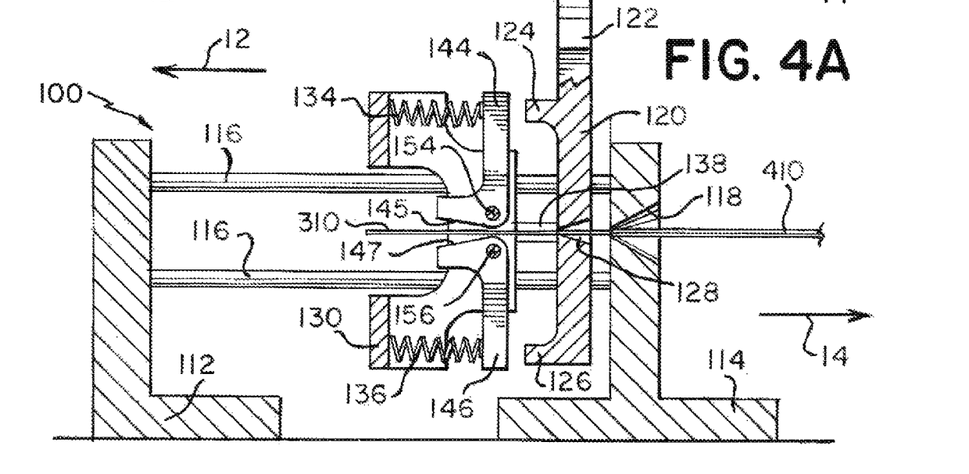
FIGS. 4A through 4D are illustrations depicting cut-away views of an exemplary retraction system executing example steps for deploying an implant according to aspects of the present invention.

FIGS. 4A through 4D are illustrations depicting cross sectional views of an exemplary retraction system 100 executing example steps for retracing a pull wire 310 from a catheter 410. FIG. 4A illustrates the exemplary retraction system 100 in an initial position such as illustrated in FIGS. 3A and 3B. The delivery catheter 410 of an implant delivery system 300 can be engaged at an entrance 118 of the retraction system 100. The pull wire 310 can be inserted through the entrance 118, through an opening 128 in the slider 120, and between clamp arms 144, 146.

The retraction system 100 can have a first clamp arm 144 with a first gripping area 145 and a second clamp arm 146 with a second gripping area 147. When the retraction system 100 is in the initial position, the pull wire 310 of an implant delivery system 300 can be positioned between the first gripping area 145 and the second gripping area 147 but not gripped by the first gripping area 145 or the second gripping area 147.

The retraction system 100 can include a slider 120 that includes a first contact 124 and a second contact 126, each contact 124, 126 can be positioned to engage each of the clamp arms 144, 146 upon movement of the slider 120 toward the clamp arms 144, 146. The contacts 124, 126 can be disengaged from the clamp arms 144, 146 when the retraction system 100 is in the initial position. The retraction system 100 can include a first spring 134 and a second spring 136 for opening the clamp arms 144, 146. When the retraction system 100 is in the initial position, the first spring 134 can be positioned to maintain the first clamp arm 144 in the open position and the second spring 136 can be positioned to maintain the second clamp arm 146 in the open position. The first clamp arm 144 can be mounted to a shuttle 130 at a first rotating joint 154, and the second clamp arm 146 can be mounted to the shuttle 130 at a second rotating joint 156. The first spring 134 and the second spring 136 can each be mounted to the shuttle 130, and the first and second springs 134, 136 can inhibit rotation of the first and second clamp arms 144, 146 about the respective rotating joints 154, 156 when the retraction system 100 is in the initial position.

The slider 120 and the shuttle 130 can each be slidably mounted to rails 116 that allow the slider 120 and the shuttle 130 to move in a distal direction 12 and a proximal direction 14, the rails 116 inhibiting movement of the slider 120 and the shuttle 130 in lateral directions orthogonal to the distal and proximal directions 12, 14. The rails 116 can extend between a distal mounting block 114 and a proximal mounting block 112. When the retraction system 100 is in the initial position, the slider 120 and the shuttle 130 can be positioned near a distal end of the rails 116, near the distal mounting block 114.

Figure 4B:
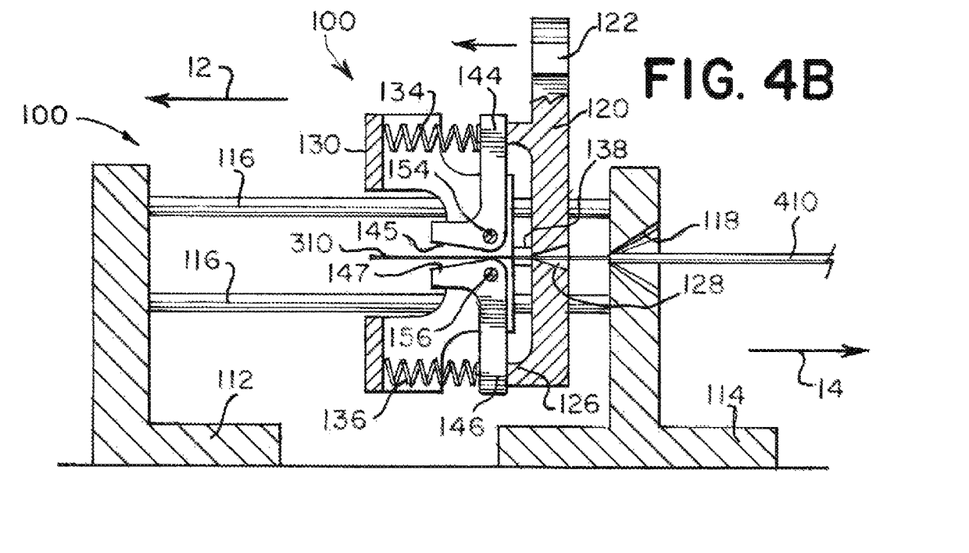
Figure 4C:
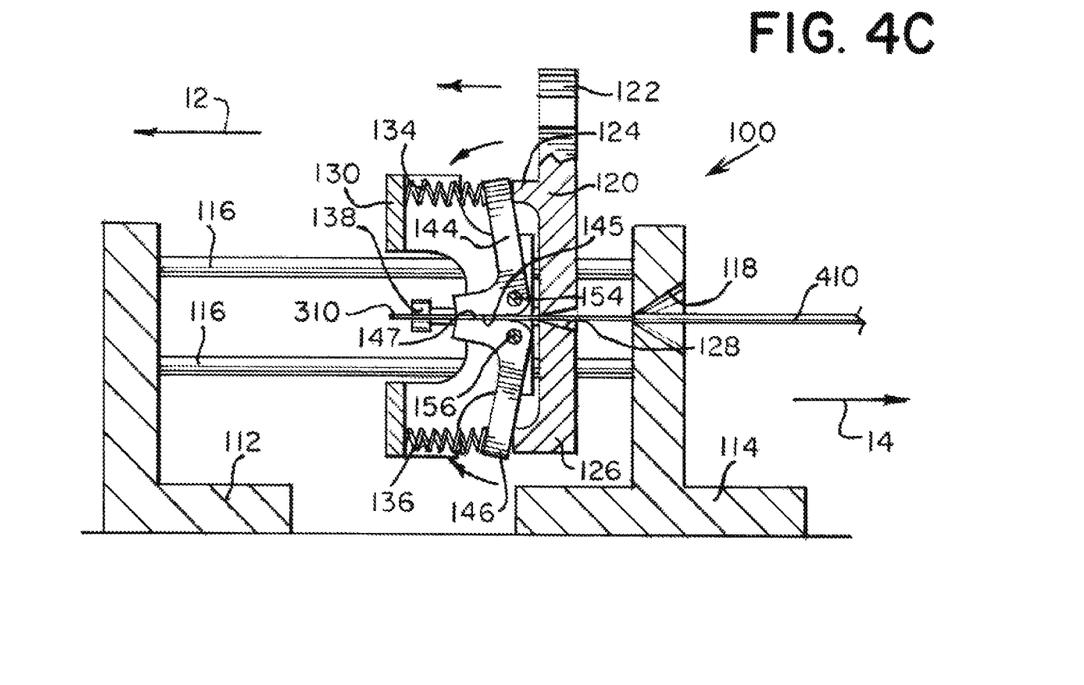
Figure 4D:
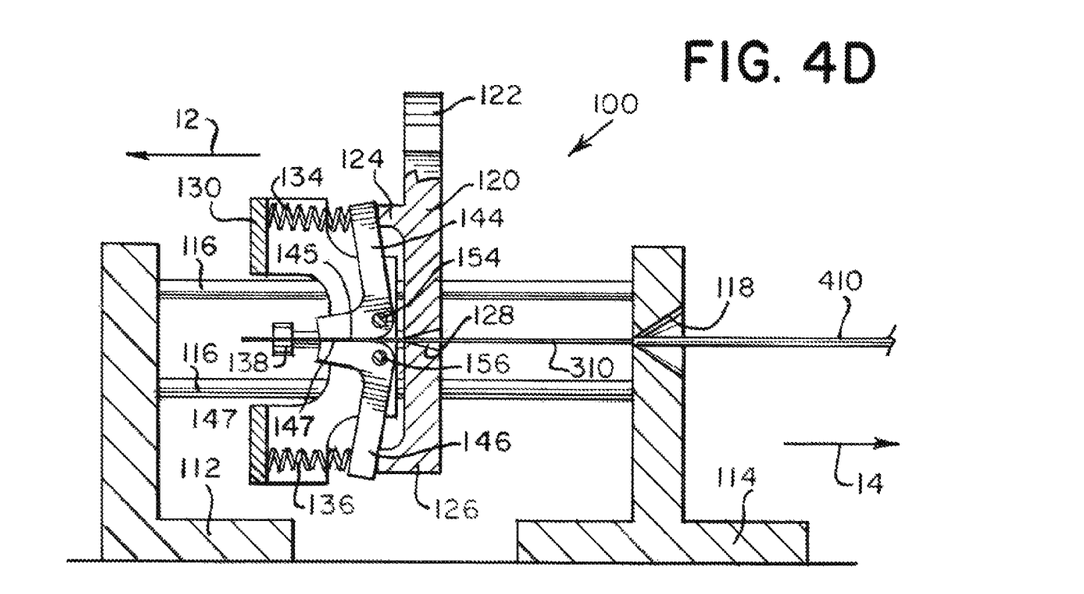

The slider 120 can include a retraction handle 122 that a user can manipulate to move the slider 120 from the initial position illustrated in FIG. 4A to the subsequent positions illustrated in FIGS. 4B through 4D. The retraction system 100 can be designed such that a user can retract the handle 122 by gripping the handle 122 and pulling the handle toward their body. Alternatively, if the retraction system 100 includes a hand-held device, the retraction system 100 can be designed such that the user grips the hand-held device with a hand while using their thumb or a finger to move a slider or a trigger that is the handle 122 on the slider 120 or a mechanism in communication with the handle 122 on the slider 120.

FIG. 4B illustrates the retraction system 100 moved from the initial position illustrated in FIG. 4A such that the slider 120 is moved in the proximal direction 12 to engage the first contact 124 on the slider 120 with the first clamp arm 144 on the shuttle 130 and to engage the second contact 126 on the slider 120 with the second clamp arm 146 on the shuttle 130. In the instant illustrated in FIG. 4B, the pair of clamp arms 144, 146 can remain in the open position such that the inner tube 310 is not engaged by the first gripping area 145 or the second gripping area 147 of the first and second clamps 144, 146, and the shuttle 130 has not moved from its initial position.

FIG. 4C illustrates the retraction system 100 moved so that the slider 120 is pulled proximally and provides a force to the pair of clamps 144, 146 that causes the clamps 144, 146 to move from the open position illustrated in FIGS. 4A and 4B to a closed position illustrated in FIG. 4C. In the closed position, the first gripping area 145 and the second gripping area 147 approach each other so that the pull wire 310 is engaged and gripped between the gripping areas 145, 147 of the pair of clamps 144, 146. The force provided by the slider 120 to the clamps 144, 146 can be sufficient to overcome the first spring force provided by the first spring 134 and the second spring force provided by the second spring 136 to cause the clamps 144, 146 to move to the closed position. A friction force between the shuttle 130 and the rails 116 can prevent the shuttle from moving as the clamps 144, 146 are opened. Additionally, or alternatively, the system 100 can include a deflecting beam over which the shuttle 130 can slide, the deflecting beam providing a controlled resistive force against which the shuttle 130 can slide. The user can translate the slider as illustrated in FIG. 4C by pulling the pull handle 122 of the slider 120. At the instant illustrated in FIG. 4C, the pull wire 310 is gripped by the pair of clamps 144, 146, but the pull wire 310 and the shuttle 130 have not moved from their initial position.

The clamps 144, 146 can have an "L" shape. The "L" shaped clamps 144, 146 can be positioned on the shuttle 130 so that the undersides of the "L" shapes are positioned opposite each other, and the upper part of the "L" shapes are positioned to be contacted by the slider 120. The respective gripping areas 145, 147 of each clamp 144, 146 can be positioned on an underside of each "L" shape. The force provided by the slider 120 to each respective clamp 144, 146 can be provided against the backside of the "L" shape near the top of the "L" shape as illustrated in FIG. 4C. Each contact 124, 126 on the slider 120 can be positioned to provide the force from the slider to the backside of each "L" shaped clamp 144, 146 near the top of each "L". Each "L" shaped contact can rotate about a rotating joint 154, 156. Each rotating joint 154, 156 can be positioned at the corner of each "L" shape. The first spring 134 and the second spring 136 can be connected to each respective "L" shape near the top of the "L" shape on the inside of the "L" shape, positioned opposite each respective contact 124, 126.

FIG. 4D illustrates the retraction system 100 with the shuttle 130 and the pull wire 310 moved proximally. Once the clamp arms 144, 146 are rotated to grip the pull wire 310 as illustrated in FIG. 4C, the shuttle 130 can begin to translate as the slider 120 is moved proximally, and the pull wire 130 can begin to be extracted from the catheter 410. The user can continue to pull the slider 120 proximally, thereby pulling the pull wire 310 out of catheter 410 until a desired distance is reached. By pulling back on the pull wire 310 while holding the catheter 410 stationary at the entrance 118 of the retractor system 100, the implant detachment step (or other such intralumenal treatment step) can be completed. When the slider 120 has reached its end of travel, the slider 120 components of the retraction system 100 can inhibit further proximal movement of the slider 120, thereby providing an indication to the user that the handle or mechanism has completed its cycle, thereby completing the treatment step. The implant (or other treatment device) can be viewed under fluoroscopy to verify that detachment (or other treatment step) has been properly completed.

Figure 4E:
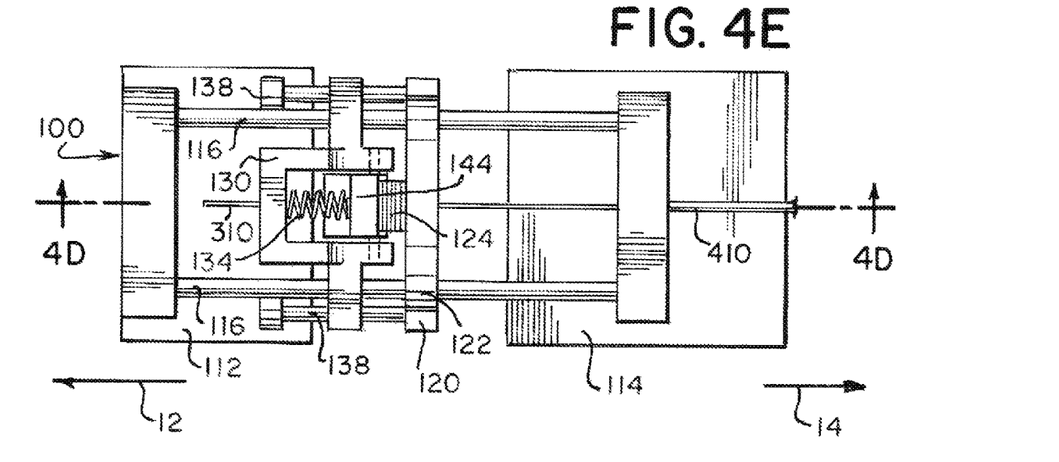
FIG. 4E is an illustration depicting a top-down view of the retraction system as positioned in FIG. 4D.

FIG. 4E illustrates the retraction system 100 in the position illustrated in FIG. 4D from a top-down view. FIG. 4D is a cross-sectional view of the system 100 illustrated in FIG. 4E as indicated in FIG. 4E.

FIGS. 5A through 5D are illustrations depicting an exemplary retraction system 100 executing example steps for releasing the pull wire 310 and returning to the initial position. After detachment of an implant is complete, a user can release pressure on a slider 120, and springs 134, 136 can automatically move clamp arms 144, 146 open, thereby releasing the clamps 144, 146 from the proximal inner tube or pull wire 310. Once the pull wire 310 is released, the shuttle 130 and slider 120 can be moved proximally to return the system 100 to a starting position without proximally translating the pull wire 310. The system 100 can be returned to the starting position manually or automatically.

Figure 5A:
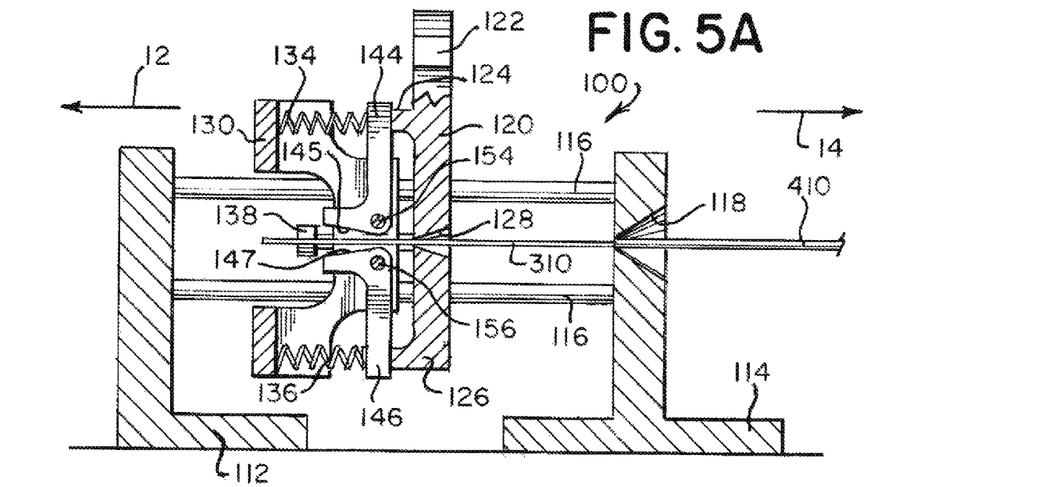
FIGS. 5A through 5D are illustrations depicting cross-sectional views and top-down views of an exemplary retraction system executing example steps for releasing a pull wire and returning to a starting position according to aspects of the present invention.

FIG. 5A is a cross-sectional view illustrating an exemplary retraction system 100 immediately after releasing a pull wire 310 following completion of the implant detachment step (or other such intralumenal treatment step). After completion of the treatment step, the user can allow a slider 120 to disengage clamps 144, 146. The user can release a retraction handle 122, and a first spring force and the second spring force can be sufficient to move the first clamp 144 and the second clamp 146 to the open position. The pull wire 310 can become disengaged by moving the pair of clamps 144, 146 from the closed position to the open position. Once the pull wire 310 is disengaged from the clamps 144, 146, a shuttle 130 and the clamps 144, 146 can be moved without moving the pull wire 310 in relation to a delivery catheter 410. FIG. 5A illustrates a first gripping area 145 and a second gripping area 147 separated to release the pull wire 310.

Figure 5B:
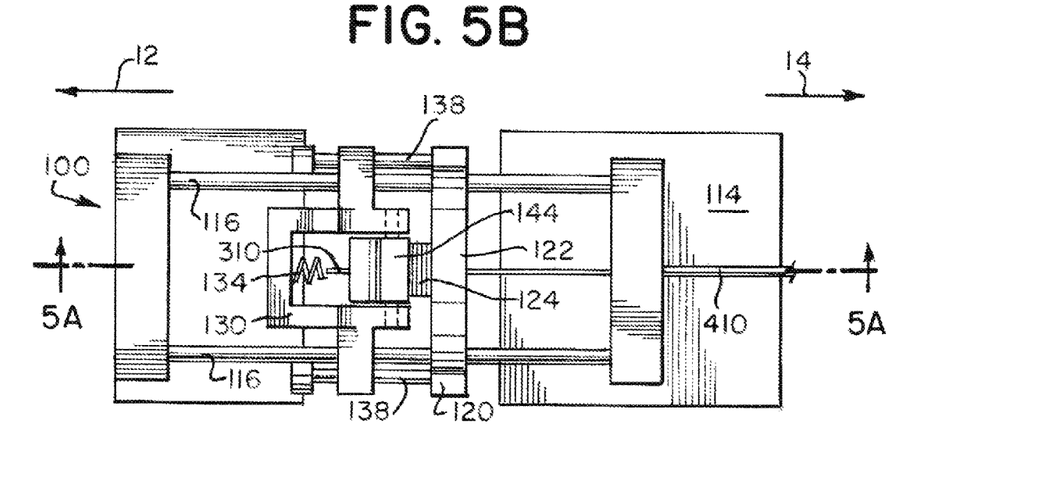

FIG. 5B illustrates the retraction system 100 positioned as illustrated in FIG. 5A from a top-down view. The retraction system 100 can include spacer pins 138 slidably mounted in the shuttle 130. As the slider 120 moves to disengage the clamps 144, the slider can move away from the shuttle 130. Each spacer pin 138 can be affixed to the slider 120 and slidably mounted with a slip fit through the shuttle 130 so that the end of each spacer pin 138 is attached to the slider 120, and each pin 138 slides through the shuttle 130 as the slider 120 moves distally away from the shuttle 130 (the slider 120 moving from a position illustrated in FIGS. 4D and 4E to a position illustrated in FIGS. 5A and 5B). This configuration can be advantageous as both the shuttle 130 and the slider 120 can be translated distally when the slider 120 is pulled distally. Heads of each spacer pin can engage the shuttle 130, and the shuttle can be dragged distally by the pins 138 when the slider is pulled distally.

Figure 5C:
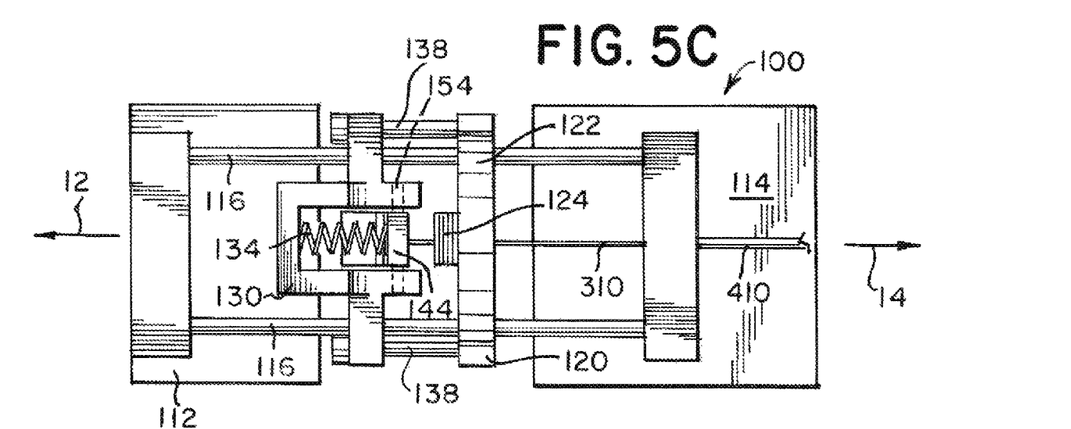

FIG. 5C is a top-down view illustrating the movement of the shuttle 130 and the slider 120 distally following release of the pull wire 310 as illustrated in FIGS. 5A and 5B. The shuttle 130 and slider 120 can be moved distally by either applying a force to each spacer pin 138 as indicated by the arrows in FIG. 5C, or by pushing the slider 120 distally via the pull handle 122. In either case, the spacer pins 138 can maintain a spacing between the shuttle 130 and the slider 120. Each spacer pin 138 can have a head that can engage the shuttle 130. The shuttle 130 can be moved distally by further providing the force against the spacer pins 138, and the spacer pins 138 can maintain a spacing between the contacts 124, 126 and the clamps 144, 146 so that the contacts 124, 126 don't engage the clamps 144, 146 as the shuttle 130 and the slider 120 are moved distally. The clamps 144, 146 can remain in the open position as the shuttle 130 and slider 120 are moved distally, and the pull wire 310 and delivery catheter 410 can maintain their extended position as the shuttle 130 and slider 120 are moved distally.

Figure 5D:
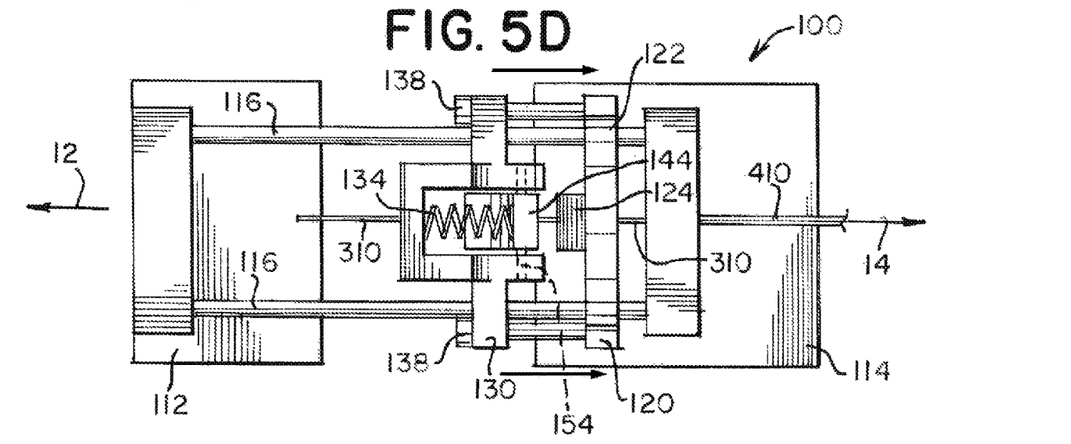

FIG. 5D illustrates the retraction system 100 returned to the initial position. The slider 120 can be slid distally along the rails 116 until it is stopped by the distal mounting block 114. The shuttle 130 can be moved distally so long as the clamps 144, 146 remain in the open position. The shuttle 130 can be moved distally until the clamps 144, 146 encounter contacts 124, 126 on the slider. The spacer pins 138 can be positioned to maintain a space between the shuttle 130 and the slider 120 so that the contacts 124, 126 do not contact the clamps 144, 146 when the shuttle 130 reaches its distal end of travel.

Figure 6:
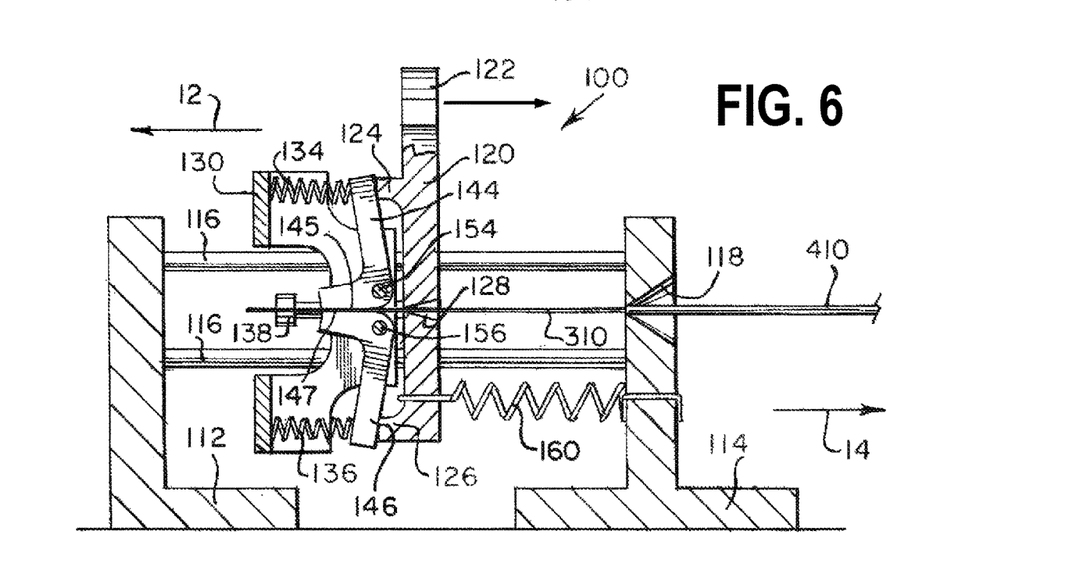
FIG. 6 is an illustration of an exemplary retraction system including a return spring according to aspects of the present invention.

FIG. 6 is an illustration of an exemplary retraction system 100 including a return spring 160. The return spring 160 can be mounted between the slider 120 and the distal mounting block 114 so that the return spring 160 provides a spring force that pulls the slider 120 distally toward the initial position or maintains the slider 120 in the initial position. The return spring 160 can be in a relaxed state when the slider 120 is in the initial position and in an extended state when the slider 120 is moved proximally from the initial position. A user can provide a force to overcome the spring force and move the slider 120 proximally then release the slider 120 to allow the return spring 160 to return the slider 120 to the initial position. As the slider 120 is first moved proximally, the slider 120 can engage the clamps 144, 146, causing the clamps 144, 146 to grip a pull wire 310, and move the shuttle 130 proximally. When the slider 120 is subsequently released, the slider 120 can disengage from the clamps 144, 146 and allow the shuttle 130 to remain in its present position while the slider 120 returns to the initial position. The retraction system 100 can be configured such that the slider 120 can be moved proximally again to engage the clamps 144, 146, grip the pull wire 310, and move the shuttle 130 through a second distance, thereby further extending the pull wire 310 from the catheter 410. Additionally, or alternatively, the system 100 can include a tension spring mounted to connect the slider 120 and the proximal mounting block 112 functional to return and/or maintain the slider 120 at the initial position.

Figure 7A:
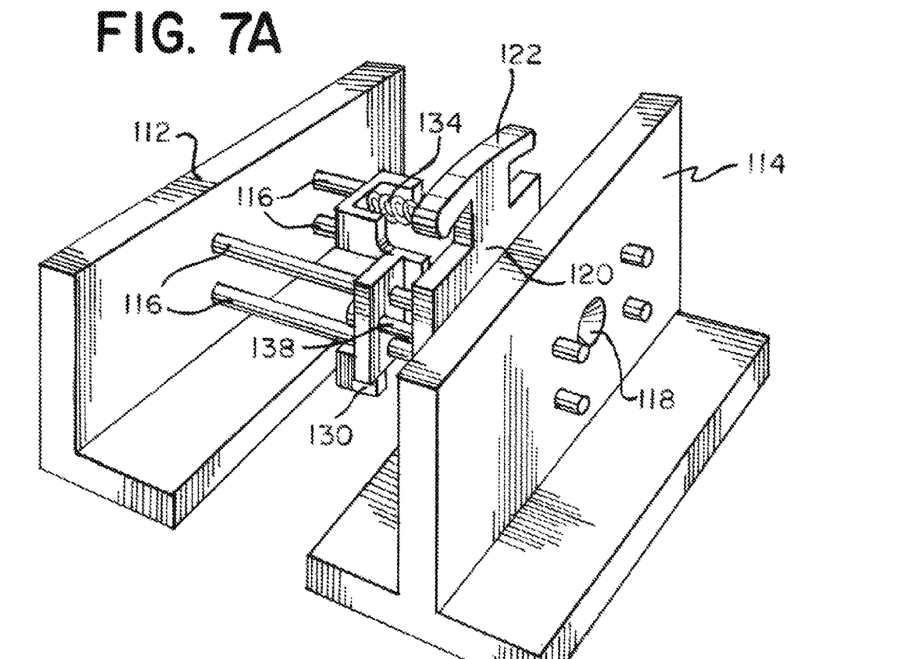
FIGS. 7A and 7B are illustrations of a top and side angled view (FIG. 7A) and a side perspective view (FIG. 7B) of an exemplary retraction system in a starting position according to aspects of the present invention.
Figure 7B:
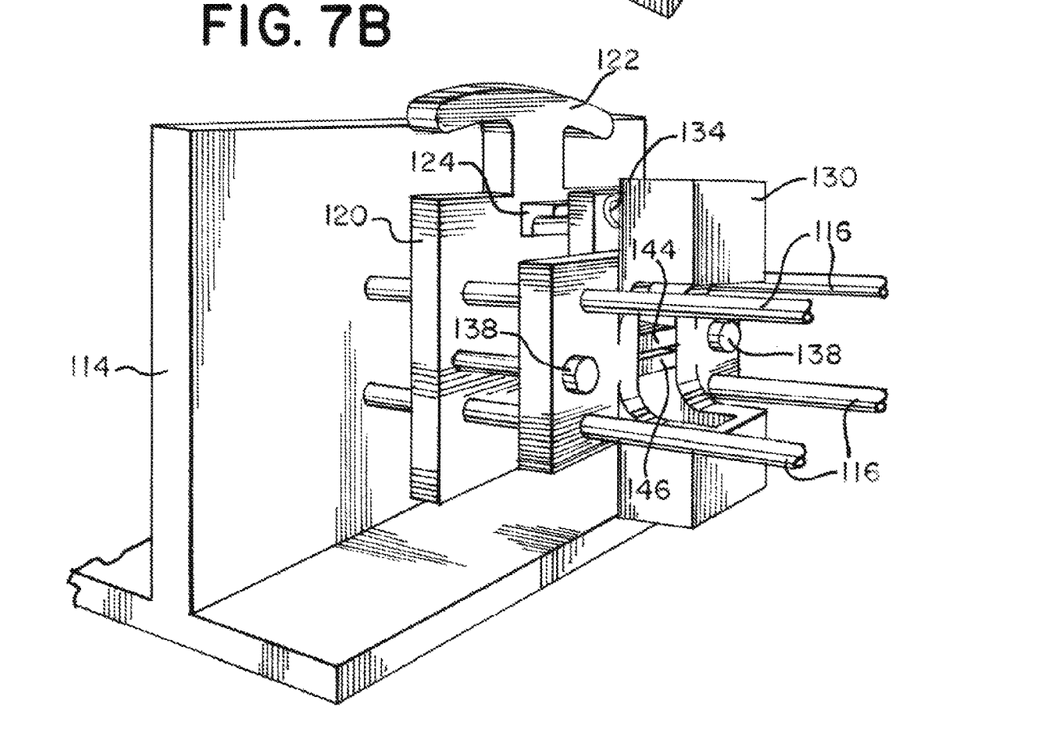

FIGS. 7A and 7B are illustrations of a top and side angled view (FIG. 7A) and a side perspective view (FIG. 7B) of an exemplary retraction system 100 in an initial position wherein the slider 120 and shuttle 130 are positioned at their distal end of travel and the clamp arms 144, 146 are open.

Figure 8A:
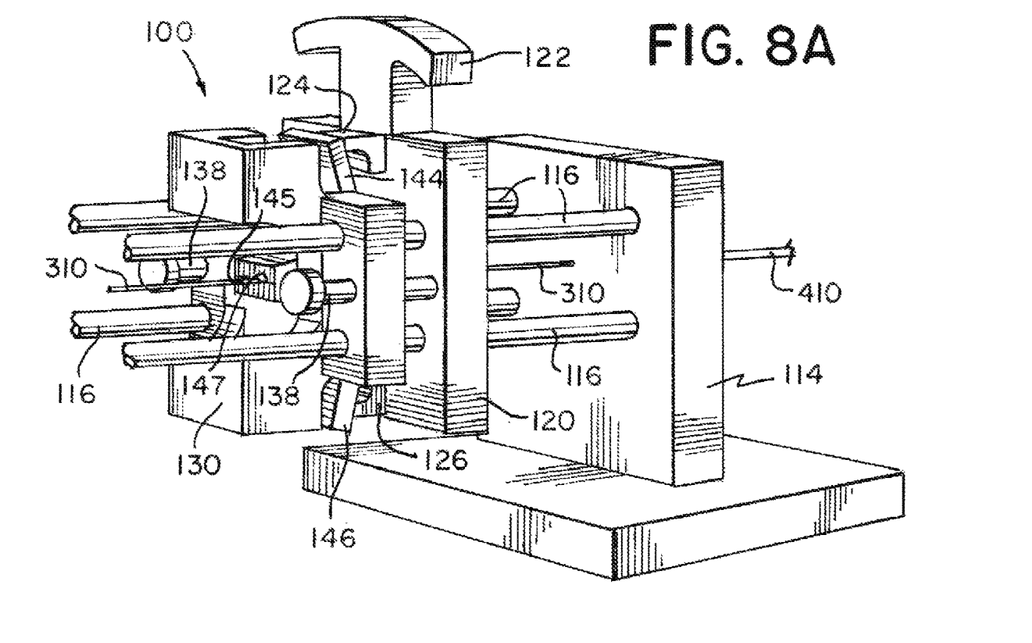
FIGS. 8A and 8B are illustrations of a side perspective view (FIG. 8A) and a top perspective view (FIG. 8B) of an exemplary retraction system having clamps in a closed position according to aspects of the present invention.
Figure 8B:
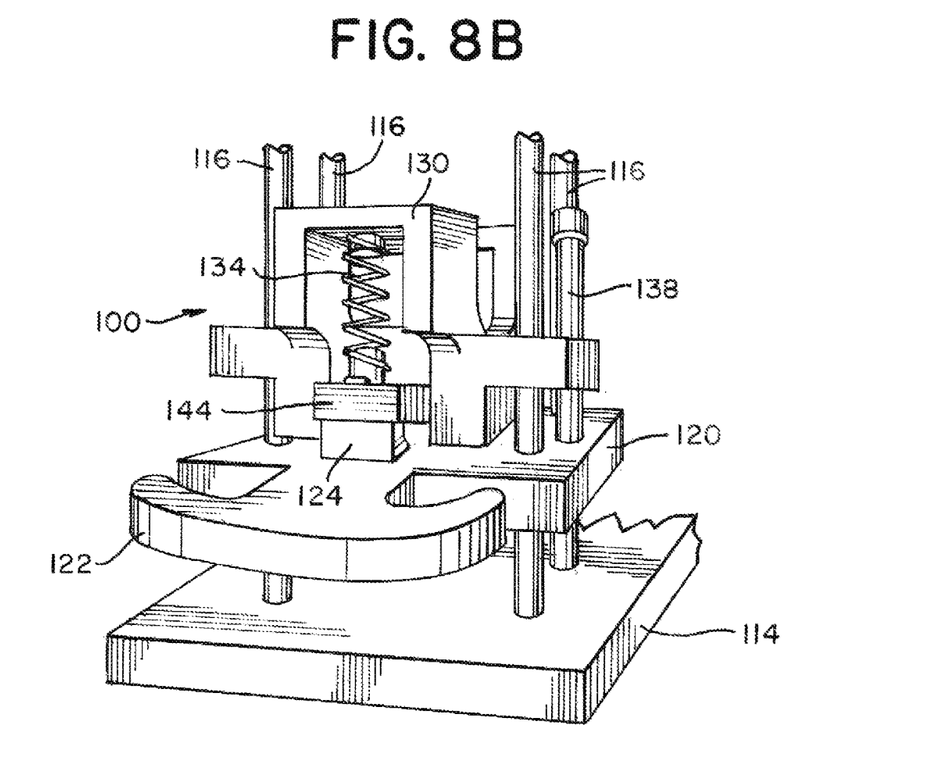

FIGS. 8A and 8B are illustrations of a side perspective view (FIG. 8A) and a top perspective view (FIG. 8B) of an exemplary retraction system 100 having clamps 144, 146 in a closed position. The system 100 can include spacer pins 138 that can be moved from an extended position as illustrated in FIGS. 7A and 7B to a retracted position as illustrated in FIGS. 8A and 8B. In the extended position, the spacer pins 138 can define a spacing between the slider 120 and shuttle 130 so that the contacts 124, 126 are separated from the clamp arms 144, 146. In the retracted position, the spacer pins can move to allow the contacts 124, 126 to engage the clamp arms 144, 146.

Figure 9A:
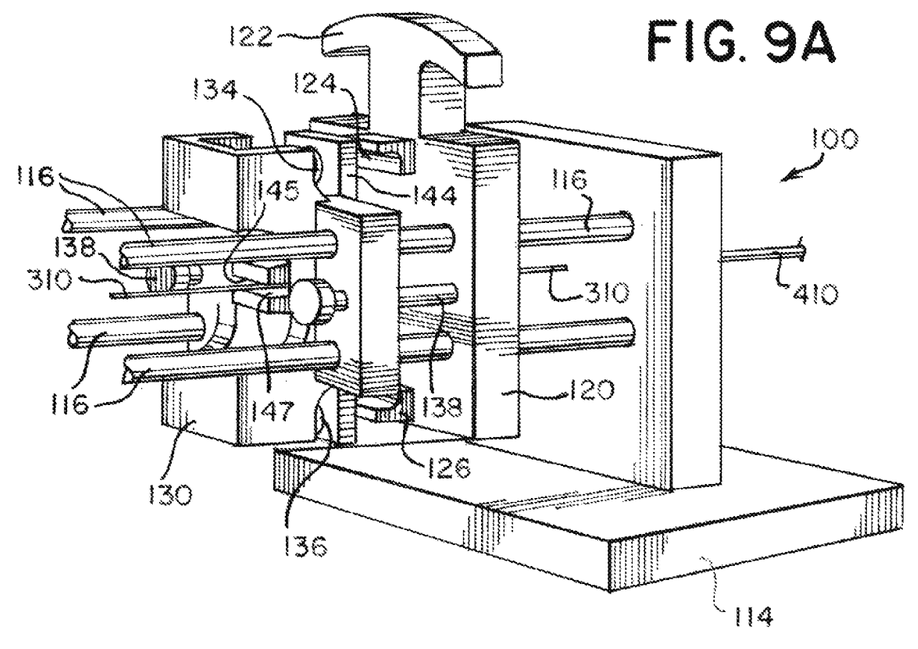
FIGS. 9A and 9B are illustrations of a side perspective view (FIG. 9A) and a top perspective view (FIG. 9B) of an exemplary retraction system having clamps in an open position according to aspects of the present invention.
Figure 9B:
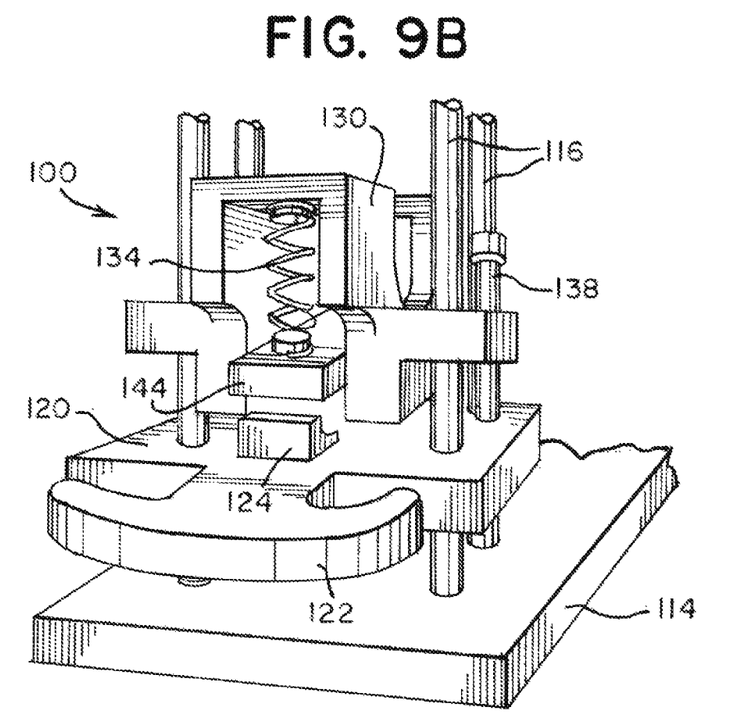

FIGS. 9A and 9B are illustrations of a side perspective view (FIG. 9A) and a top perspective view (FIG. 9B) of an exemplary retraction system 100 having contacts 124, 126 in contact with clamps 144, 146 and the clamps 144, 146 in an open position. The retraction system 100 can include spacer pins 138 attached to the slider 120 and slidably mounted through the shuttle 130. As the slider 120 moves from a position as illustrated in FIGS. 8A and 8B to a position as illustrated in FIGS. 9A and 9B, the pins 138 can slide through the shuttle 138.

Figure 10A:
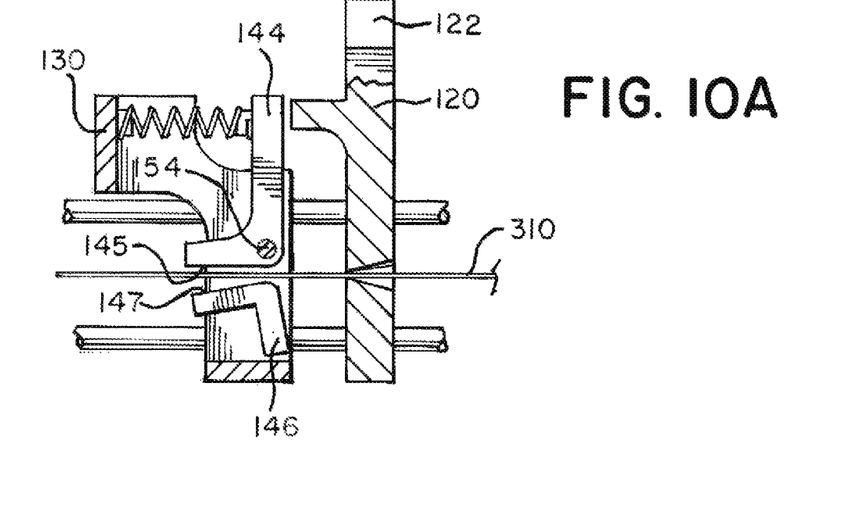
FIGS. 10A and 10B are illustrations of a pair of clamp arms including one rotatable clamp arm and one non-rotating clamp arm in an open position (FIG. 10A) and a closed position (FIG. 10B) according to aspects of the present invention.
Figure 10B:
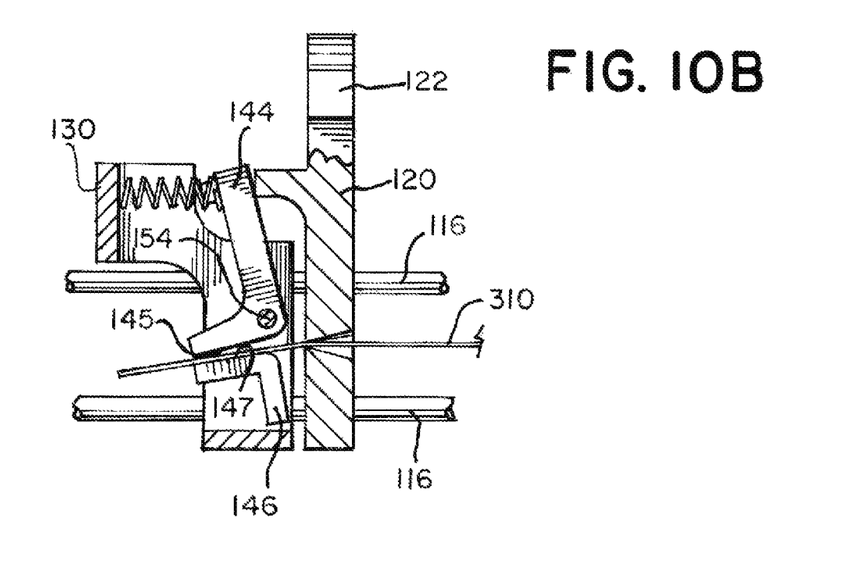

FIGS. 10A and 10B are illustrations of an alternative configuration of a pair of clamp arms 144, 146 for a retraction system 100. The pair of clamp arms 144,146 can include one rotatable clamp arm 144 and one non-rotating clamp arm 146. FIG. 10A illustrates the clamp arms 144, 146 in an open position. The rotating clamp arm 144 can be mounted to a shuttle 130 at a joint 154 and can rotate about the joint 154. The non-rotating clamp 146 can be affixed to the shuttle so that it translates proximally and distally together with the shuttle 130 and does not move in relation to the shuttle 130.

FIG. 10B illustrates the clamp arms 144, 146 in the closed position. The slider 120 can contact the rotating clamp arm 144, causing it to rotate and approach the non-rotating clamp arm 146 so that the pair of clamp arms 144, 146 grips a pull wire 310. The non-rotating clamp arm 146 can be out of plane with the pull wire 320 so that when the rotating clamp arm 144 is rotated, the pull wire 310 is slightly bent. Configured thusly, in some configurations, the pull wire 310 can engage a larger gripping area 147 on the non-rotating clamp arm 146 compared to examples utilizing two rotating clamp arms and can thereby have a comparative increased grip strength.

The descriptions contained herein are examples of embodiments of the invention and are not intended in any way to limit the scope of the invention. As described herein, the invention contemplates many variations and modifications of the retraction system, including alternative geometries for component parts, alternative materials for construction, alternative means for mounting movable components, alternative means for incorporating the retraction system into a retractor or larger device, etc. These modifications would be apparent to those having ordinary skill in the art to which this invention relates and are intended to be within the scope of the claims which follow.

The invention claimed is:

1. A retraction system for withdrawing an inner elongated member of an implantation delivery system from a catheter, the retraction system comprising:
   a first clamp comprising a first gripping area;
   a second clamp comprising a second gripping area;
   a shuttle translatable in a proximal direction and a distal direction, on which the first clamp and the second clamp are mounted; and
   a slider translatable in the proximal direction and the distal direction, the slider comprising a first contact and a second contact,
     wherein a first translation of the slider in the proximal direction translates the first contact proximally to apply a first force from the first contact to the first clamp, the first force moving the first clamp from an open position to a closed position, wherein, in the open position, the first gripping area and the second gripping area are positioned to allow the inner elongated member of the implantation delivery system to pass through, wherein, in the closed position, the first gripping area and the second gripping area are positioned to engage the inner elongated member, wherein a second translation of the slider in the proximal direction proximally translates the first clamp and the second clamp to proximally withdraw the inner elongated member from the catheter of the implantation delivery system while holding the catheter in place, wherein the first translation of the slider translates the second contact proximally to apply a second force from the second contact to the second clamp, the second force moving the second clamp from the open position to the closed position, and wherein the first and second contacts engage and/or disengage the first and second clamps simultaneously.

2. The retraction system of claim 1 further comprising:
a distal mounting block;
a proximal mounting block; and
a rail extending between the distal mounting block and the proximal mounting block, the shuttle and the slider each slidably mounted on the rail.

3. The retraction system of claim 2,
wherein the distal mounting block further comprises a first opening for receiving the implantation delivery system, and wherein the first opening is sized to inhibit proximal movement of the catheter and to allow the inner elongated member to pass through.

4. The retraction system of claim 2 further comprising:
a return spring in communication with the slider and the distal mounting block for applying a return spring force sufficient to move the slider in the distal direction.

5. The retraction system of claim 1,
wherein a third translation of the slider in the distal direction moves the first contact to disengage the first clamp.

6. The retraction system of claim 5 further comprising:
a first spring positioned to apply a first spring force on the first clamp, the first spring force being sufficient to move the first clamp from the closed position to the open position when the first contact is disengaged from the first clamp.

7. The retraction system of claim 6 further comprising:
a second spring positioned to apply a second spring force on the second clamp, the second spring force being sufficient to move the second clamp from the closed position to the open position when the second contact is disengaged from the second clamp.

8. The retraction system of claim 1,
wherein the first clamp is rotatable about a first rotating joint and is attached to the shuttle at the first rotating joint.

9. The retraction system of claim 8,
wherein the first force from the first contact produces a first rotation of the first clamp about the first rotating joint.

* * * * *